(12) United States Patent
Nordman

(10) Patent No.: US 6,890,336 B2
(45) Date of Patent: May 10, 2005

(54) SURGICAL CUTTER WITH MODULAR BLADES

(75) Inventor: Mark Nordman, Burket, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 110 days.

(21) Appl. No.: 10/141,895

(22) Filed: May 9, 2002

(65) Prior Publication Data

US 2003/0212401 A1 Nov. 13, 2003

(51) Int. Cl.[7] .............................................. A61B 17/00
(52) U.S. Cl. ..................................................... 606/80
(58) Field of Search ............................... 606/53, 79, 80, 606/81, 82, 83, 84, 86; 409/232, 234; 279/8; 408/67; 30/347

(56) References Cited

U.S. PATENT DOCUMENTS

| | | | | |
|---|---|---|---|---|
| 4,116,200 A | | 9/1978 | Braun et al. ................. 128/305 |
| 4,811,632 A | * | 3/1989 | Salyer .......................... 76/115 |
| 4,922,612 A | * | 5/1990 | Greenwood ................. 30/166.3 |
| 5,100,267 A | | 3/1992 | Salyer .......................... 407/54 |
| 5,295,992 A | | 3/1994 | Cameron ...................... 606/79 |
| 5,299,893 A | | 4/1994 | Salyer et al. .................. 407/54 |
| 5,501,686 A | | 3/1996 | Salyer .......................... 606/79 |
| 5,632,747 A | * | 5/1997 | Scarborough et al. ........ 606/79 |
| 5,709,688 A | * | 1/1998 | Salyer .......................... 606/81 |
| 5,968,049 A | | 10/1999 | Da Rold ....................... 606/80 |
| 5,976,143 A | | 11/1999 | McCue ......................... 606/80 |
| 5,976,148 A | | 11/1999 | Charpenet et al. ............ 606/91 |
| 6,245,074 B1 | | 6/2001 | Allard et al. .................. 606/80 |
| 6,471,724 B2 | * | 10/2002 | Zdeblick et al. .......... 623/17.16 |
| 2003/0135219 A1 | * | 7/2003 | Salyer et al. .................. 606/81 |

* cited by examiner

Primary Examiner—Cary E. O'Connor
Assistant Examiner—Anu Ramana
(74) Attorney, Agent, or Firm—Taylor & Aust, P.C.

(57) ABSTRACT

A surgical cutter for use as an orthopedic reamer includes a shaft, a head, a modular blade member and a threaded retainer member. The shaft has a shaft end and a shaft bore located in the shaft end, at least a portion of the shaft bore being threaded. The head is coupled with the shaft proximate the shaft end, the head being configured for retaining debris. The modular blade member is mounted on the head, the modular blade having a primary blade surface and at least one blade tooth extending from the primary blade surface. The primary blade surface is substantially planar, and the modular blade member further has a centrally located blade mounting hole therein. The threaded retainer member extends through the blade mounting hole and operatively mating with the shaft bore, and the threaded retainer member further includes a retainer edge at a distal end thereof. The retainer edge is biased against the primary blade surface proximate the blade mounting hole.

13 Claims, 4 Drawing Sheets

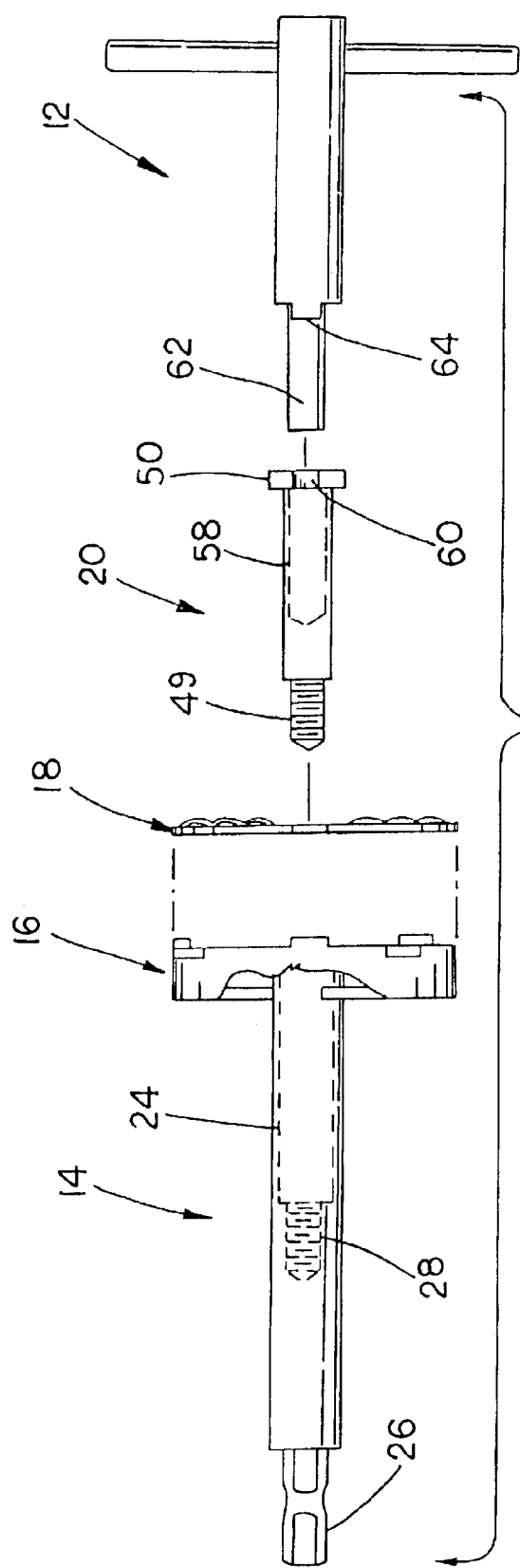
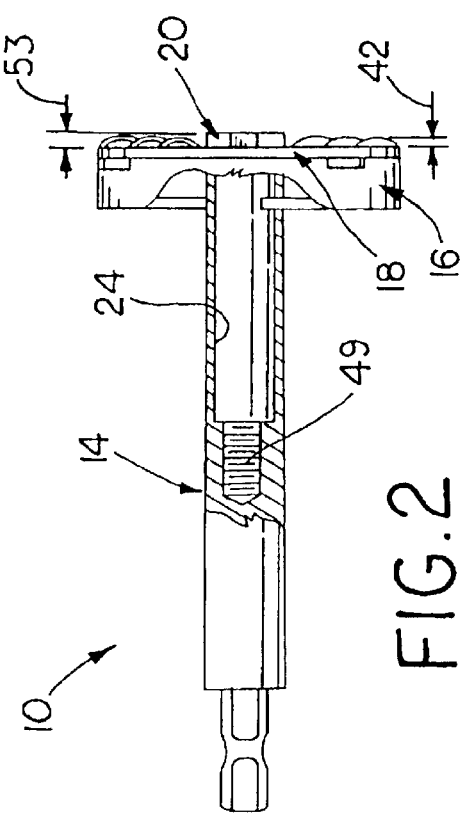

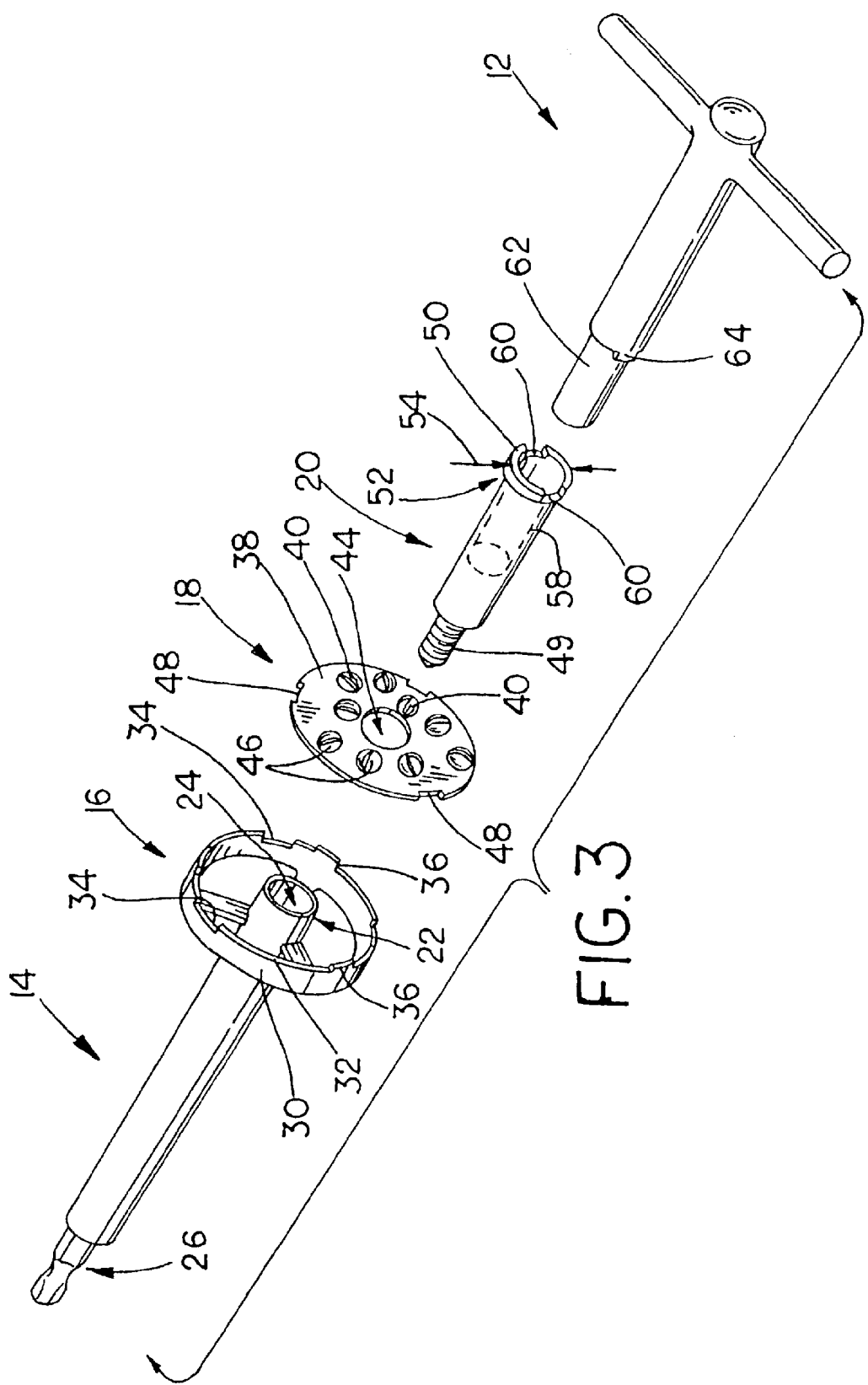

SURGICAL CUTTER WITH MODULAR BLADES

BACKGROUND OF THE INVENTION

1. Field of the Invention

The present invention relates to surgical cutters, and, more particularly, to orthopaedic surgical cutters

2. Description of the Related Art

Calcar planars are surgical tools which are typically used for planing the proximal femur. However, customizable sizes for use in smaller joints (shoulder, great toe, ankle), pediatrics or revision surgery can be produced. A calcar planar reamer is typically composed of a reamer cup mounted on a shaft, which in turn is mounted in the chuck or collet of a portable drill or other powered shaft Calcar planars cups have an arrangement of precisely shaped cutting surfaces extending outwardly therefrom. Such calcar planar reamer cups are typically separable from their respective shafts to allow for changing cup size prior to or during surgery, cleaning and/or sharpening Orthopedic reamers and cutters must be formed and operated in such a manner so as to minimize any risk of causing contamination during their use in surgery Consequently, prior orthopedic reamer cups and cutters have needed to be cleaned after each use and/or made disposable. Due to the costs of such tools, disposability of such tools has not proven to be a very economical option in many cases.

What is needed in the art is a calcar planar surgical cutter that includes a blade portion (the part most subject to wear and most likely to be changed during use) that is readily changeable and disposable, thereby permitting reuse of the other portions of the cutter after disposal of a given blade member.

SUMMARY OF THE INVENTION

The present invention provides a surgical cutter for use as an orthopedic reamer that is modular in nature, providing a head capable of retaining bone and other debris and a thin, disposable blade member that can be removably mounted upon the head.

The invention comprises, in one form thereof, a surgical cutter for use as an orthopedic reamer that includes a shaft, a head, a modular blade member and a threaded retainer member The shaft has a shaft end and a shaft bore located in the shaft end, at least a portion of the shaft bore being threaded. The head is coupled with the shaft proximate the shaft end, the head being configured for retaining debris The modular blade member is mounted on the head, the modular blade having a primary blade surface and at least one blade tooth extending from the primary blade surface The primary blade surface is substantially planar, and the modular blade member further has a centrally located blade mounting hole therein. The threaded retainer member extends through the blade mounting hole and operatively mating with the shaft bore, and the threaded retainer member further includes a retainer edge at a distal end thereof. The retainer edge is biased against the primary blade surface proximate the blade mounting hole.

An advantage of the present invention is that the modular nature permits the debris-retaining head to be continuously reused for retaining debris produced during cutting yet permitting frequent changing of the blade member, as needed.

Another advantage is that the disposable blade members can be readily and precisely produced via a process employing a laser cutting step and a punch pressing step.

Yet another advantage is the cylindrical wall portion of the debris-retaining head minimizes bone spray and permits capture of bone fragments (for possible reuse in bone grafting).

An even further advantage is the combination of the threaded retainer member and the precision central hole within each of the shaft and blade member acts to accurately center the blade member relative to the shaft and thereby promote flat, accurate planing of a bone A yet additional advantage is that the disposable blade member includes a spiral, overlapping pattern of D-shaped holes, the spiral pattern and D-shaped holes each promoting a flat, accurate cutting action. The D-shaped holes further aid in the physical removal and gathering bone chips and help to break bone chips into desirable particle sizes for grafting.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2 is a partial cut-away, side view of the surgical cutter shown in FIG. 1;

FIG. 3 is an exploded view of the combination of the surgical cutter and driver tool shown in FIG. 1, FIG. 4 is an exploded, side view of the combination of the surgical cutter and driver tool shown in FIG. 1.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
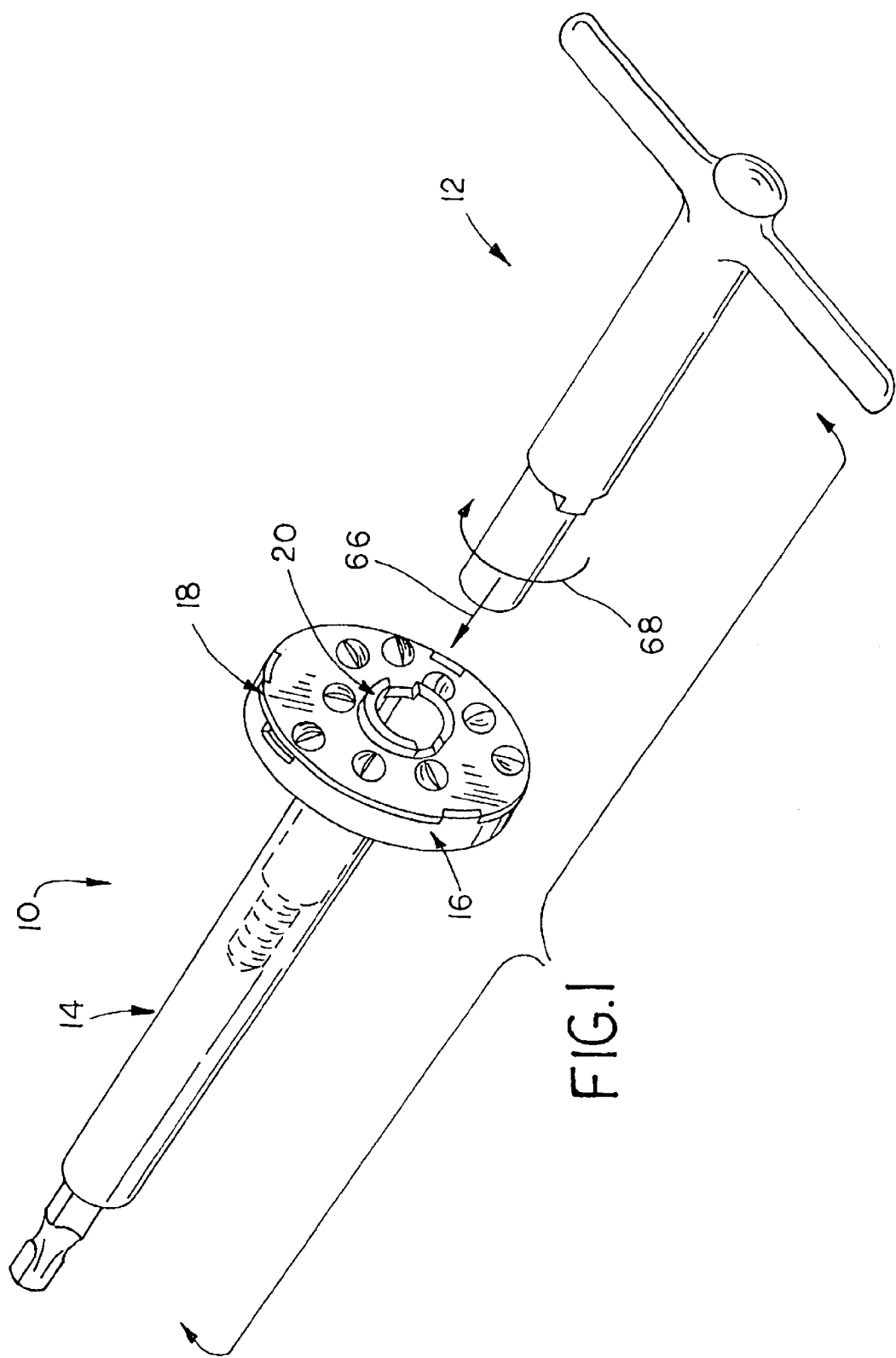
FIG. 1 is a perspective view of an embodiment of the surgical cutter of the present invention along with a driver tool used in the assembly thereof.

Referring now to the drawings, and more particularly to FIG. 1, there is shown a surgical cutter 10 for use as an orthopedic reamer and a driver tool 12 for aiding in the assembly thereof. Surgical cutter 10 is a calcar planar design capable of retaining debris generated during use thereof Surgical cutter 10, as further seen from FIG. 2 and shown in exploded form in FIG. 3, generally includes a shaft 14, a head 16, a modular blade member 18 and a threaded retainer member 20.

Shaft 14 has a shaft end 22 and a shaft bore 24 located in shaft end 22. Opposite shaft end 14 is a collet end 26 configured for engaging a rotary driver member (not shown). Shaft bore 24 includes, at least in part, a threaded bore portion 28 (FIG. 4)

Head 16 is coupled with shaft 14 proximate shaft end 22, head 16 being configured for retaining debris. Head 16 can be coupled with shaft 14 in a manner so as to be one of detachably connected, permanently attached (e.g., via welding or brazing) and integrally formed therewith. Head 16 includes a debris retaining wall member 30, debris retaining wall member 30 being substantially cylindrical in shape and positioned so as to be substantially concentric with shaft 14. Debris retaining wall member 30 includes a wall edge 32 upon which modular blade member 18 is mounted. Wall edge 32 is provided with at least one of a wall slot 34 and a wall tab 36 to facilitate positioning of modular blade member 18 thereon.

Figure 5:
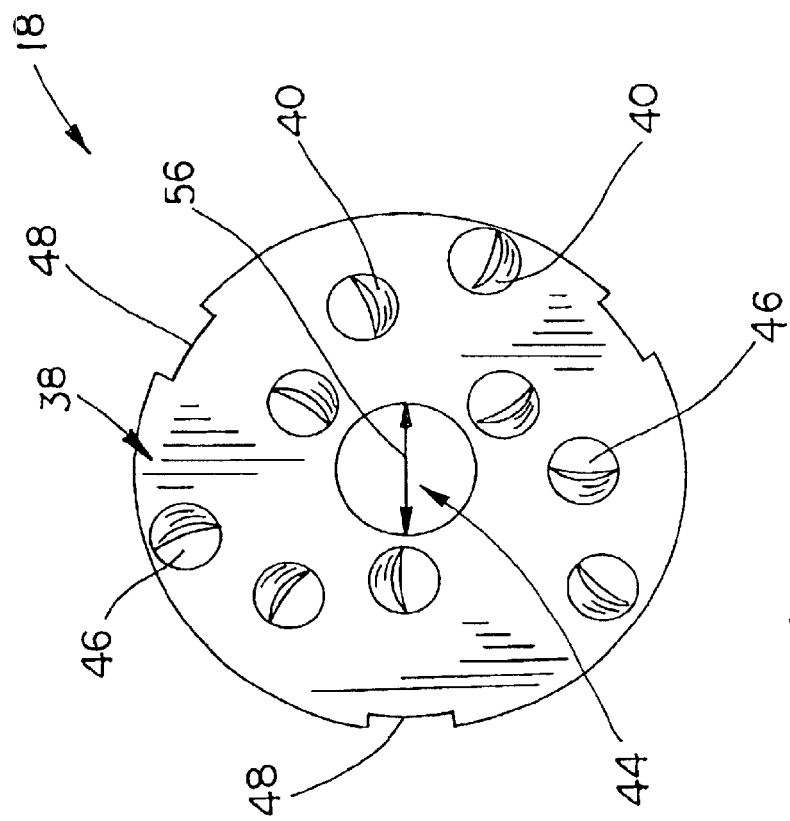
FIG. 5 is a top view of the modular blade member of this embodiment of the present invention.

Modular blade member 18 is mounted on debris retaining wall member 30 of head 16 As best seen from FIGS. 2 and 5, modular blade member 18 has a primary blade surface 38 and at least one blade tooth 40 extending therefrom. Each blade tooth 40 has a maximum tooth height 42 relative to primary blade surface 38 Primary blade surface 38 is substantially planar, and modular blade member 18 further has a centrally located blade mounting hole 44 therein.

Primary blade surface 38 has at least one blade hole 46 therein, each blade tooth 40 having one blade hole 46 corresponding thereto. Each blade hole 46 and blade tooth 40 corresponding thereto together define a D-shape for each blade hole 46. In the embodiment illustrated, a plurality of blade holes 46 and corresponding blade teeth 40 are associated with primary blade surface 38. Advantageously, blade teeth 46, and thereby blade holes 46, are distributed in a generally spiral pattern (as best seen in FIG. 5) across primary blade surface 38 to promote a flat, accurate cutting action.

Modular blade member 18 is provided with at least one of a blade member tab (not shown) and a blade member slot 48. Each one of a blade member tab and blade member slot 48 opposes and matingly fits with a corresponding one of wall slot 34 and wall tab 36. Such a combination greatly minimizes, if not prevents, the rotation of modular blade member 18 relative to head 16

Threaded retainer member 20 extends through blade mounting hole 44 and into shaft bore 24 and operatively mates, via retainer threading 49 thereof, with threaded bore portion 28 of shaft bore 24. Threaded retainer member 20 further includes a retainer edge 50 at a distal end 52 opposite retainer threading 49. Retainer edge 50 is biased against primary blade surface 38 proximate blade mounting hole 44. Retainer edge 50 extends above primary blade surface 38 a maximum edge distance 53 of no more than approximately 0.03 inches in excess of maximum tooth height 42.

Retainer edge 50 has an edge diameter 54, while blade mounting hole 44 has a mounting hole diameter 56 Edge diameter 54 is greater than mounting hole diameter 56 in order to facilitate the holding of modular blade member 18 with threaded retainer member 20.

Furthermore, threaded retainer member 20 has a central retainer bore 58 therein, and retainer edge 50 thereof has a pair of diametrically opposed edge slots 60 therein Retainer bore 58 and the pair of edge slots 60 are conjunctively configured for operatively receiving driver tool 12 therein.

Driver tool 12 is configured for releasably driving threaded retainer member 20 into shaft bore 24 within shaft end 22. Driver tool 12 includes a tool post 62 and at least one tool tab 64. Tool post 62 is configured for insertion (as indicated schematically by insertion arrow 66 in FIG. 1) into retainer bore 58 of threaded retainer member 20. Each tool tab 64 is configured for operatively engaging in a respective edge slot 60 of retainer edge 50. Such engagement thereby allows driver tool 12 to transfer rotary movement (as indicated schematically by rotation arrow 68 in FIG. 1) thereof to threaded retainer member 20 This rotary movement, thereby, can be used to engage or disengage, as necessary, threaded retainer member 20 with or from threaded bore portion 28 of shaft bore 24, as appropriate.

In assembling surgical cutter 10, modular blade member 18 is mounted on head 16. Threaded retainer member 20 is extended through blade mounting hole 44 and into shaft bore 22 within shaft end 22 Retainer threading 49 of threaded retainer member 20 is engaged with threaded bore portion 28 of shaft bore 24 in a manner so as to thereby threadedly connect threaded retainer member 20 with shaft 14. Eventually, retainer edge 50 is biased against primary blade surface 38 proximate blade mounting hole 44. When biased as such, retainer edge 50 extends above primary blade surface 38 a maximum distance of no more than approximately 0.03 inches in excess of maximum tooth height 42.

The combined steps of extending threaded retainer member 20 through blade mounting hole 44 and into shaft bore 22 and of engaging retainer threading 49 with threaded bore portion 28 further include a number of substeps. Tool post 62 of driver tool 12 is inserted into retainer bore 58 in threaded retainer member 20. Each tool tab 64 is fitted into a respective edge slot 60 of retainer edge 50. Tool driver 12 is rotated, each tool tab 64 thereby operatively engaging a respective edge slot 60 to thereby also cause rotation of threaded retainer member 20. Such rotation of threaded retainer member 20 enables retainer threading 49 to operatively enjoin threaded bore portion 28 of shaft bore 24.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical cutter for use as an orthopedic reamer, said surgical cutter comprising:

a shaft having a shaft end and a threaded shaft bore located in said shaft end;

a head coupled with said shaft proximate said shaft end, said head including a debris retaining member, said debris retaining member including a wall edge;

a modular blade member mounted on said wall edge, said modular blade having a primary blade surface and at least one blade tooth extending from said primary blade surface, said primary blade surface being substantially planar, said modular blade member further having a centrally located blade mounting hole therein; and a threaded retainer member extending through said blade mounting hole and operatively mating with said threaded shaft bore, said threaded retainer member further including a retainer edge at a distal end thereof, said retainer edge biased against said primary blade surface proximate said blade mounting hole, said threaded retainer member including a central retainer bore extending past said modular blade.

2. The surgical cutter of claim 1, wherein each said blade tooth has a maximum tooth height relative to said primary blade surface, said retainer edge extending above said primary blade surface a maximum edge distance of no more than approximately 0.03 inches in excess of said maximum tooth height.

3. A surgical cutter for use as an orthopedic reamer, said surgical cutter comprising:

a shaft having a shaft end and a shaft bore located in said shaft end, at least a portion of said shaft bore being threaded;

a head coupled with said shaft proximate said shaft end, said head being configured for retaining debris;

a modular blade member mounted on said head, said modular blade having a primary blade surface and at least one blade tooth extending from said primary blade surface, said primary blade surface being substantially planar, said modular blade member further having a centrally located blade mounting hole therein; and a threaded retainer member extending through said blade mounting hole and operatively mating with said shaft bore, said threaded retainer member further including a retainer edge at a distal end thereof, said retainer edge biased against said primary blade surface proximate said blade mounting hole, said threaded retainer member including a central retainer bore extending past said modular blade.

4. The surgical cutter of claim 3, wherein each said blade tooth has a maximum tooth height relative to said primary blade surface, said retainer edge extending above said primary blade surface a maximum edge distance of no more than approximately 0.03 inches in excess of said maximum tooth height.

5. The surgical cutter of claim 3, wherein said head includes a debris retaining wall member, said debris retaining wall member beings substantially cylindrical.

6. The surgical cutter of claim 3, wherein said primary blade surface has at least one blade hole therein, each said blade tooth having one said blade hole corresponding thereto.

7. The surgical cutter of claim 6, wherein each said blade hole and said blade tooth corresponding thereto together form a D-shape.

8. The surgical cutter of claim 6, further comprising a plurality of said blade holes, said blade holes being distributed in a generally spiral pattern across said primary blade surface.

9. The surgical cutter of claim 3, wherein said retainer edge has an edge diameter, said blade mounting hole having a mounting hole diameter, said edge diameter being greater than said mounting hole diameter.

10. The surgical cutter of claim 3, wherein said retainer edge having a pair of diametrically opposed edge slots therein, said retainer bore and said pair of edge slots conjunctively configured for operatively receiving a driver tool therein, said driver tool being configured for releasably driving said threaded retainer member into said shaft bore.

11. A surgical cutter for use as an orthopedic reamer, said surgical cutter comprising:
   a shaft having a shaft end and a threaded shaft bore located in said shaft end;
   a head coupled with said shaft proximate said shaft end, said head including a debris retaining member, said debris retaining member including a wall edge, said head includes a debris retaining wall member, said debris retaining wall member being a substantially cylindrical;
   a modular blade member mounted on said wall edge, said modular blade having a primary blade surface and at least one blade tooth extending from said primary blade surface, said primary blade surface being substantially planar, said modular blade member further having a centrally located blade mounting hole therein, wherein said wall edge is provided with at least one of a wall slot and a wall tab, said modular blade member being provided with a corresponding at least one of a blade member tab and a blade member slot, each said corresponding one of a blade member tab and a blade member slot opposing and matingly fitting with a corresponding said one of a wall slot and a wall tab; and
   a threaded retainer member extending through said blade mounting hole and operatively mating with said threaded shaft bore, said threaded retainer member further including a retainer edge at a distal end thereof, said retainer edge biased against said primary blade surface proximate said blade mounting hole, said threaded retainer member including a central retainer bore extending past said modular blade.

12. A method of assembling a surgical cutter, said method comprising the steps of:
   providing a shaft having a shaft end and a shaft bore located in said shaft end, at least a portion of said shaft bore having a threaded bore portion therein, said shaft having a head coupled therewith proximate said shaft end, said head being configured for retaining debris;
   mounting a modular blade member on said head, said modular blade having a primary blade surface and at least one blade tooth extending from said primary blade surface, each said blade tooth having a maximum tooth height relative to said primary blade surface, said modular blade member further having a centrally located blade mounting hole therein;
   providing a threaded retainer member having a retainer threading and a retainer edge associated therewith, said retainer edge being located at a distal end of said threaded retainer member opposite said retainer threading thereof, said retainer edge having a retainer edge diameter, said blade mounting hole having a mounting hole diameter, said retainer edge diameter being greater than said mounting hole diameter, said threaded retainer member including a central retainer bore extending past said modular blade;
   extending said threaded retainer member through said blade mounting hole and into said shaft bore;
   engaging said retainer threading with said bore threading of said shaft bore in a manner so as to thereby threadedly connect said threaded retainer member with said shaft; and
   biasing said retainer edge against said primary blade surface proximate said blade mounting hole, said retainer edge extending above said primary blade surface a maximum edge distance of no more than approximately 0.03 inches in excess of said maximum tooth height.

13. The method of claim 12, wherein said retainer edge having at least one edge slot therein, said method further including the step of providing a driver tool, said driver tool including a tool post, said tool post having at least one tool tab thereon, said tool post being configured for insertion into said retainer bore of said threaded retainer member, each said tool tab being configured for operatively engaging in a respective said edge slot of said retainer edge, said extending step and said engaging step combined including the substeps of:
   inserting said tool post of said driver tool into said retainer bore;
   fitting each said tool tab into a respective said edge slot of said retainer edge;
rotating said tool driver, each said tool tab of said tool driver operatively engaging a respective said edge slot to thereby also cause rotation of said threaded retainer member, said rotation of said threaded member enabling said retainer threading to operatively enjoin said threaded bore portion of said shaft bore.

* * * * *

UNITED STATES PATENT AND TRADEMARK OFFICE
CERTIFICATE OF CORRECTION

PATENT NO. : 6,890,336 B2
DATED : May 10, 2005
INVENTOR(S) : Nordman

It is certified that error appears in the above-identified patent and that said Letters Patent is hereby corrected as shown below:

Title page,
Item [57], ABSTRACT,
Line 6, after "debris", insert -- . --;
Line 9, after "surface", insert -- . --;

Column 1,
Line 15, between "shaft" and "Calcar", insert -- . --;
Line 42, between "member" and "The", insert -- . --;
Line 45, between "debris" and "The", insert -- . --;
Line 48, between "surface" and "The", insert -- . --;

Column 2,
Line 67, between "16" and "As", insert -- . --;

Column 3,
Line 40, between "therein" and "Retainer", insert -- . --; and
Line 53, between "20" and "This", insert -- . --.

Signed and Sealed this

Twenty-fourth Day of January, 2006

JON W. DUDAS
*Director of the United States Patent and Trademark Office*